United States Patent [19]

Demosthene et al.

[11] 4,266,057

[45] May 5, 1981

[54] PROCESS FOR THE PREPARATION OF 2-ISOPROPYLAMINO PYRIMIDINE

[75] Inventors: Claude G. Demosthene, Aramon; Christian R. Aspisi, Boulbon, both of France

[73] Assignee: Expansia, Paris, France

[21] Appl. No.: 47,477

[22] Filed: Jun. 11, 1979

[30] Foreign Application Priority Data

Jun. 16, 1978 [NZ] New Zealand .................. 187595

[51] Int. Cl.³ .................................... C07D 239/42
[52] U.S. Cl. ............................................. 544/330
[58] Field of Search ................................. 544/330

[56] References Cited

U.S. PATENT DOCUMENTS 3,984,414 10/1976 Esanu .................................. 544/330
4,073,895 2/1978 Esanu .................................. 544/330

OTHER PUBLICATIONS

Kaye et al., Rec. Trav. Chim., 71, pp. 309–317, (1952), QD1R3.

*Primary Examiner*—Paul M. Coughlan, Jr.
*Attorney, Agent, or Firm*—Eyre, Mann, Lucas & Just

[57] ABSTRACT

The invention relates to the preparation process of 2-isopropylamino pyrimidine consisting in reaction at room temperature, 2-amino pyrimidine on acetone in the presence of an organic carboxylic acid, and of an excess of an alkaline borohydride.

1 Claim, No Drawings

PROCESS FOR THE PREPARATION OF 2-ISOPROPYLAMINO PYRIMIDINE

The present invention relates to a new improved process for the preparation of 2-isopropylamino pyrimidine presenting the advantage of a one step reaction together with an increased yield compared with the previously known processes for the preparation of 2-isopropylamino pyrimidine for 2-amino pyrimidine.

It is also known to prepare 2-isopropylamino pyrimidine from 2-chloro pyrimidine and isopropylamine; this was described by BROWN D. J. et HARPER J. S. J.Chem. Soc. 5542 (1965).

Only one reductive alkylation-according to the authors-seems to have been effected for the preparation of 2-alkylamino pyrimidine from 2-amino pyrimidine by using formic acid; see I. A. KAYE et I. C. KOGON Rec. Trav. Chim. 71, 309, (1952).

2-isopropylamino pyrimidine may also be prepared by alkylation of 2-amino pyrimidine by alkyl halogenide, which leads to 2-alkyl 1,2-dihydro 2-imino pyrimidines that in basic conditions turn into the corresponding 2-alkylamino pyrimidines by DIMROTH rearrangement (BROWN D. J. et PADDON-ROW M. N. J.Chem. Soc. (C) 903 (1967). However, all those well-known methods give 2-isopropylamino pyrimidine with a generally poor yield, under 50%.

According to the present invention, it has been established that 2-isopropylamino pyrimidine may be obtained with a very good yield by reacting 2-amino pyrimidine on acetone in the presence of an organic carboxylic acid and of an excess of an alcaline borohydride. In this reaction, acetone is both one of the reagents and the solvent; accordingly, a large excess of acetone is necessary.

The invention will be better understood from the following example:

In a 2-liter reactor fitted with stirring, heating and cooling means, there are poured a solution of 9.5 g (0.1 mol) of 2-amino pyrimidine in 100 ml of anhydrous acetone and 100 ml of crystallizable acetic acid; the reaction mixture is maintained at room temperature or preferably some degrees lower.

Under stirring, there is slowly added, while maintaining the temperature in the same range, 10 g (0.26 mol) of sodium borohydride and stirring is maintained for 5 hours after the end of the addition, at room temperature.

There is just added 150 ml of an aqueous ammoniac solution at 20%, the temperature being maintained at about 30° C.; 100 ml of chloroform are added and after addition of 50 ml of water and stopping of the stirring, there is obtained a solution in two phases; the chloroform phase is separated and the aqueous solution is washed twice by, at each time, 100 ml of chloroform. All the chloroform phases are gathered, washed with an aqueous ammoniac solution, then by water until neutrality is reached and finally dried on sodium sulphate.

There is just obtained 4 g (yield 60%) of 2-isopropylamino pyrimidine of high purity which is confirmed by analysis.

We claim:

1. A method for the preparation of 2-isopropylamino pyrimidine comprising reacting at room temperature 2-amino pyrimidine with a large excess of acetone in the presence of an organic carboxylic acid and an alkali metal borohydride.

* * * * *